US012564502B2

(12) United States Patent
Colvin et al.

(10) Patent No.: US 12,564,502 B2
(45) Date of Patent: Mar. 3, 2026

(54) PROSTHETIC FOOT

(71) Applicant: WillowWood Global LLC, Mount Sterling, OH (US)

(72) Inventors: James M. Colvin, Hilliard, OH (US); Matthew M. Wernke, Tampa, FL (US); Evandro M. Ficanha, Grove City, OH (US)

(73) Assignee: WILLOWWOOD GLOBAL LLC, Mount Sterling, OH (US)

( * ) Notice: Subject to any disclaimer, the term of this patent is extended or adjusted under 35 U.S.C. 154(b) by 878 days.

(21) Appl. No.: 17/509,864

(22) Filed: Oct. 25, 2021

(65) Prior Publication Data

US 2022/0039971 A1     Feb. 10, 2022

Related U.S. Application Data

(63) Continuation-in-part of application No. 16/808,796, filed on Mar. 4, 2020, now Pat. No. 11,173,053.

(51) Int. Cl.
*A61F 2/66* (2006.01)
*A61F 2/50* (2006.01)

(52) U.S. Cl.
CPC ........ *A61F 2/66* (2013.01); *A61F 2002/5053* (2013.01); *A61F 2002/6664* (2013.01)

(58) Field of Classification Search
CPC ................ A61F 2/66; A61F 2002/6664; A61F 2002/6621; A61F 2002/6642; A61F 2002/6657
See application file for complete search history.

(56) References Cited

U.S. PATENT DOCUMENTS

| 4,822,363 A | | 4/1989 | Phillips | |
| 5,314,282 A | | 5/1994 | Murphy et al. | |
| 5,361,483 A | * | 11/1994 | Rainville | .......... B29C 66/72141 |
| | | | | 411/908 |

(Continued)

FOREIGN PATENT DOCUMENTS

EP          2785286 B1     5/2020

OTHER PUBLICATIONS (PCT), U.S. Patent and Trademark Office (ISA/US), International Search Report and Written Opinion, International Application No. PCT/US2022/047094, 11 pages, Feb. 28, 2023.

(Continued)

*Primary Examiner* — Bruce E Snow
(74) *Attorney, Agent, or Firm* — Thompson Hine LLP

(57)          ABSTRACT

A prosthetic foot that includes a foot plate having a toe portion and a heel portion, a shank plate bonded to the foot plate along a seam that extends from the toe portion rearward toward the heel portion to terminate at an end, the shank plate separated from the foot plate forming a gap between the foot plate and shank plate extending rearward from the end of the seam; and an attachment structure attaching the foot plate to the shank plate, wherein the attachment structure includes fibers extending continuously through the shank plate, the gap, and the foot plate. In embodiments, the foot plate and shank plate are made of composite material and the attachment structure alternately extends through the seam and through a flexible material between the shank plate and the foot plate.

9 Claims, 8 Drawing Sheets

(56)                        References Cited

U.S. PATENT DOCUMENTS

| | | | | |
|---|---|---|---|---|
| 6,527,811 | B1 * | 3/2003 | Phillips ..................... | A61F 2/66 |
| | | | | 623/55 |
| 7,351,022 | B2 | 4/2008 | Denslow | |
| 7,419,509 | B2 | 9/2008 | Christensen | |
| 8,900,326 | B2 | 12/2014 | Doddroe et al. | |
| 2005/0125985 | A1 | 6/2005 | Adams et al. | |
| 2006/0069450 | A1 | 3/2006 | McCarvill et al. | |
| 2007/0100465 | A1 | 5/2007 | Egan | |
| 2010/0332002 | A1 * | 12/2010 | Nelson ...................... | A61F 2/66 |
| | | | | 264/319 |
| 2016/0061245 | A1 | 3/2016 | Toyozumi et al. | |
| 2016/0158030 | A1 | 6/2016 | Doddroe et al. | |
| 2016/0287411 | A1 * | 10/2016 | Lindhe ..................... | A61F 2/66 |
| 2018/0296370 | A1 | 10/2018 | Jonsson et al. | |
| 2020/0375765 | A1 | 12/2020 | Friesen et al. | |
| 2021/0275327 | A1 | 9/2021 | Colvin et al. | |
| 2022/0039971 | A1 * | 2/2022 | Colvin ..................... | A61F 2/66 |

OTHER PUBLICATIONS

European Patent Office, Extended European Search Report, issued Aug. 20, 2025, which pertains to European Patent Application No. 22887954.0. 7 pages.

* cited by examiner

PROSTHETIC FOOT

STATEMENT OF FEDERALLY FUNDED RESEARCH

This invention was made with government support under 2R42HD093476-02A1 awarded by the National Institutes of Health; Eunice Kennedy Shriver National Institute of Child Health& Human Development. The government has certain rights in the invention.

TECHNICAL FIELD

The disclosure relates to prosthetic limbs for humans, and more particularly, to a prosthetic foot.

BACKGROUND

A conventional prosthetic foot design may have structural components including a foot plate with a toe portion, a heel portion, and an intermediate portion with an arched configuration that flexes under the weight of the user as needed throughout the gait cycle. The structural components also may include a shank plate in addition to the foot plate. The shank plate typically has a vertical upper portion for connection with another prosthetic device such as, for example, a prosthetic knee or a socket. The shank plate also may have a lower portion with a curvature reaching forward from the upper portion. The lower portion of the shank plate flexes under the weight of the user and is fastened to the foot plate to transmit the weight load forces to the foot plate.

Although such designs are lightweight and relatively inexpensive to fabricate, they may be subject to failure after repeated use when the connection between the shank plate and the foot degrades or separate. Also, such designs may be difficult to customize to suit the needs of a user. Accordingly, there is a need for a robust, easily customized prosthetic foot.

SUMMARY

The disclosed prosthetic foot structure provides a relatively simple and cost-effective design that is easily customized to provide optimal comfort during use. The disclosed prosthetic foot structure is relatively simple to fabricate and yet provides a robust and rugged product.

In an exemplary embodiment, a prosthetic foot, a foot plate having a toe portion and a heel portion; a shank plate bonded to the foot plate along a seam that extends from the toe portion rearward toward the heel portion to terminate at an end, the shank plate separated from the foot plate forming a gap between the foot plate and shank plate extending rearward from the end of the seam; and an attachment structure attaching the foot plate to the shank plate, wherein the attachment structure includes fibers extending through the shank plate, the gap, and the foot plate.

In another embodiment, a prosthetic foot includes a foot plate having a toe portion and a heel portion; a shank plate bonded to the foot plate along a seam that extends from the toe portion rearward toward the heel portion to terminate at an end, the shank plate separated from the foot plate forming a gap between the foot plate and shank plate extending rearward from the end of the seam; and an attachment structure attaching the foot plate to the shank plate, wherein the attachment structure includes a central shaft of fibers extending through the first shank, the seam, and the foot plate; wherein an end of the seam is transversely aligned along a length of the prosthetic foot with a rearmost trailing edge of the central shaft.

In yet another embodiment, a method of making a prosthetic foot includes placing a first layer of peel ply material on a sole mold part, placing a first layer of composite weave on the first layer of peel ply material, placing a foot plate on the first layer of composite weave, the foot plate having a toe portion and a heel portion, placing second and third layers of peel ply material over and under a heel mold part, and placing a strip of flexible material over a portion of the second layer of peel ply material. A shank plate is placed over the portion of the second layer of peel ply material and the strip of flexible material, and an attachment structure is inserted through the shank plate, the strip of flexible material, the portion of the second layer of the peel ply material, and the foot plate. The attachment structure includes fibers extending through the shank plate, the flexible material, and the foot plate. The method also includes placing a second layer of composite weave on a top surface of the shank plate, placing a fourth layer of peel ply material over the second layer of composite weave, and placing an upper mold part over the fourth layer of peel ply material.

The first layer of peel ply material, the first layer of composite weave, the foot plate, second and third layers of peel ply material, the strip of flexible material, the shank plate, the second layer of composite weave, the a fourth layer of peel ply material, and the attachment structure are compressed between the upper mold part, the heel mold part, and the sole mold part to bond the shank plate to the foot plate to form a seam therebetween that extends forward of the attachment structure toward the toe portion. The attachment structure includes fibers extending through the shank plate, the strip of flexible material, and the foot plate, thereby forming a flared top portion that overlies a top surface of the shank plate and a flared bottom portion that overlies a bottom surface of the foot plate. The method also includes forming a gap between the shank plate and the foot plate that extends rearward of the flexible strip toward the heel portion.

Other objects and advantages of the disclosed composite prosthetic foot structure will be apparent from the following description, the accompanying drawings, and the appended claims.

BRIEF DESCRIPTION OF THE DRAWINGS

FIG. 4 is an enlarged view of the attachment structure of the composite prosthetic foot structure of FIG. 1;

DETAILED DESCRIPTION

Figure 1:
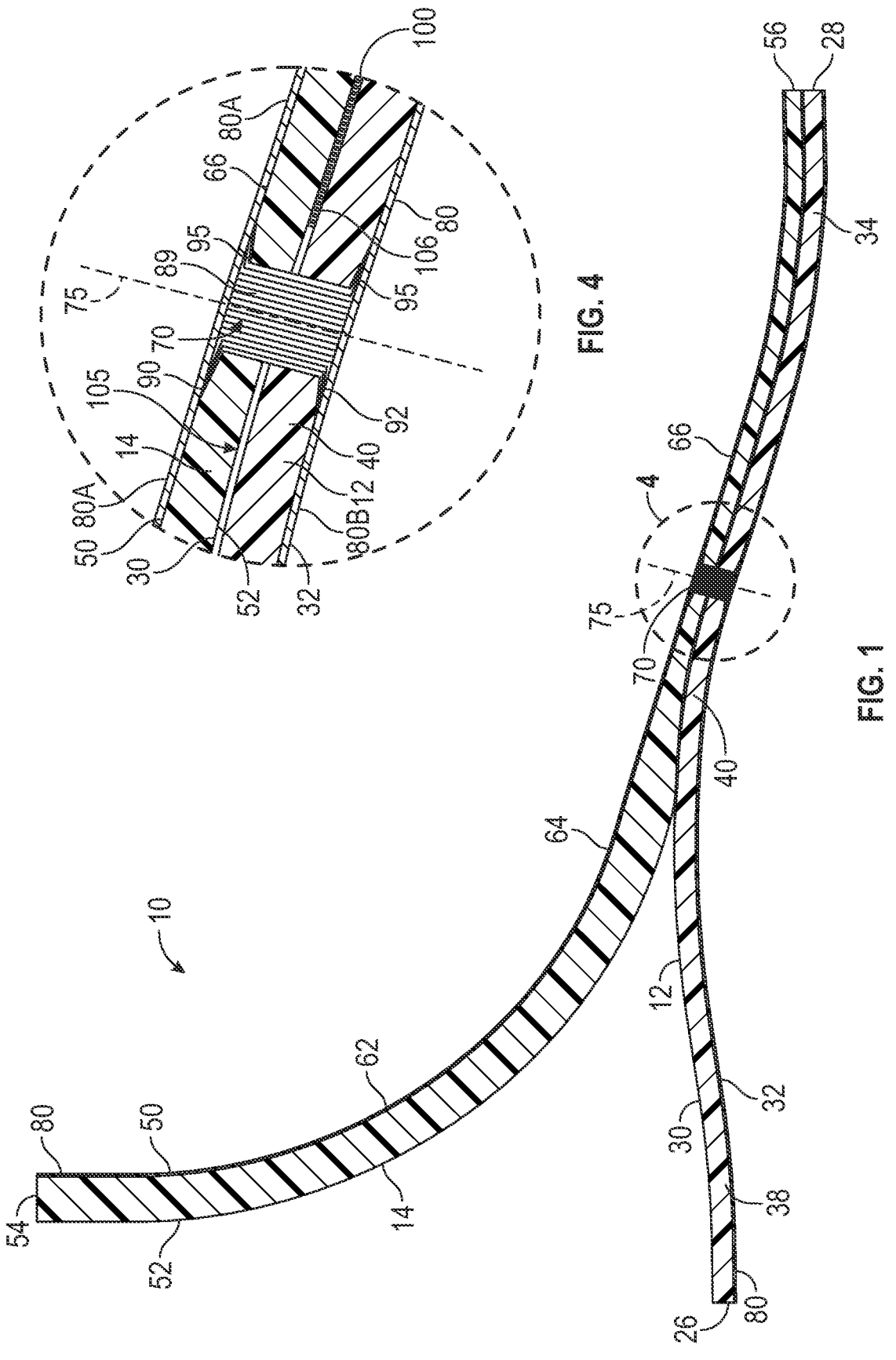
FIG. 1 is a side view in section of an exemplary embodiment of the disclosed composite prosthetic foot structure.

The structures illustrated in the drawings include parts that are examples of the structural elements recited in the claims. One or more elements of one embodiment may be used in combination with, or as a substitute for, one or more elements of another as needed for any implementation of the claimed invention.

As shown in FIG. 1, an exemplary embodiment of the disclosed prosthetic foot, generally designated 10, includes a plate assembly comprising a foot plate 12 and a shank plate 14. The prosthetic foot 10 is adapted to be combined with other parts (not shown) of a complete prosthetic foot system. Such other parts may include, for example, a cosmetic foot shell. The foot plate 12 and the shank plate 14 both have strength and stiffness as needed to support the user's weight and have flexibility as needed to serve as springs for comfort and assistance in the heel-strike and toe-off stages of the user's gait cycle.

Figure 2:
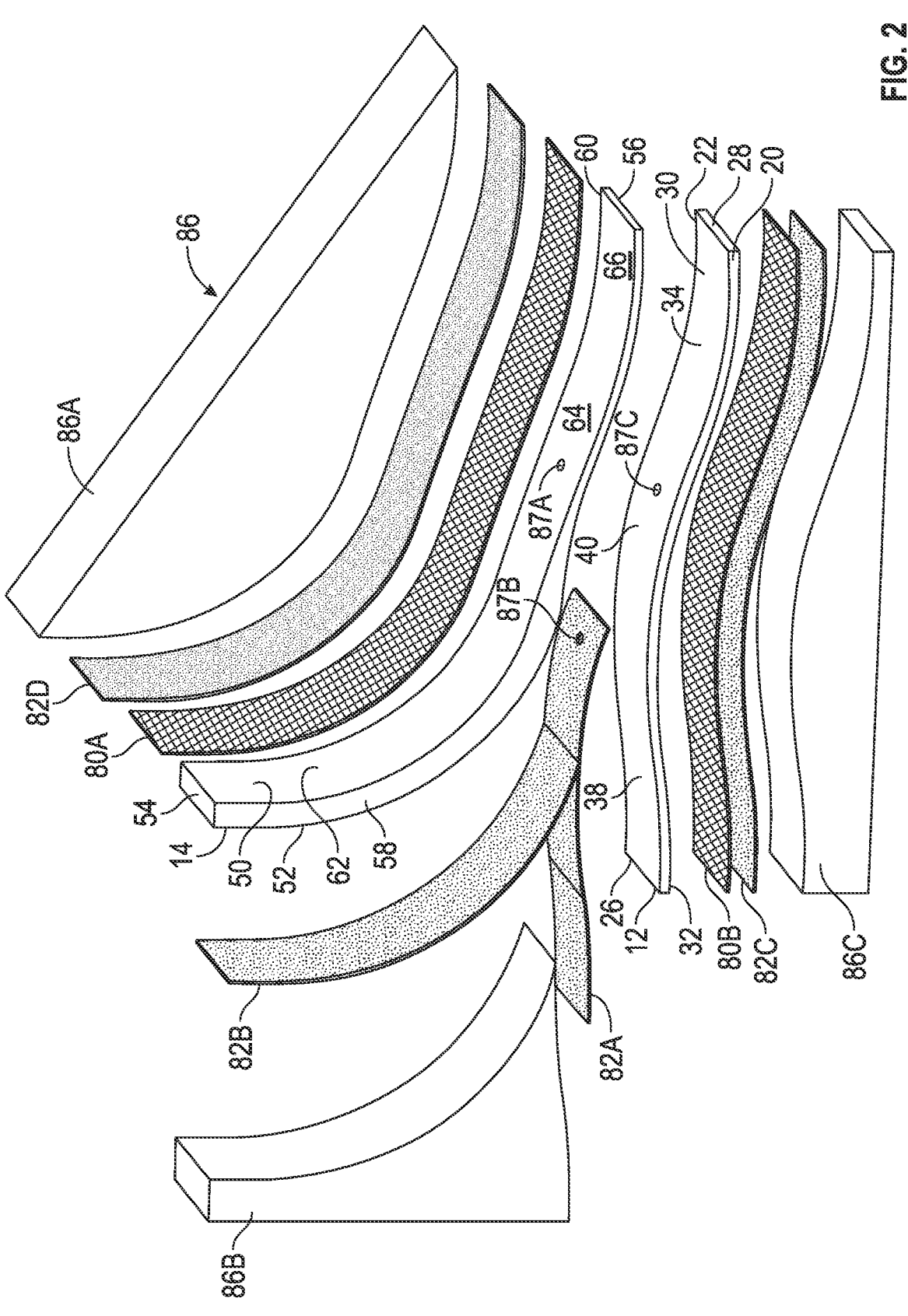
FIG. 2 is an exploded view showing additional parts of the prosthetic foot structure of FIG. 1, shown between mold parts.

As shown in FIGS. 1 and 2, in embodiments the foot plate 12 has a narrow, elongate shape with opposing side edges 20 and 22 reaching longitudinally between opposing end edges 26 and 28. Top and bottom side surfaces 30 and 32, respectively, define the length of the foot plate 12 between the opposing end edges 26 and 28, as well as the width of the foot plate 12 between the opposing side edges 20 and 22. In embodiments, the top and bottom side surfaces 30 and 32 have contours defining generally distinct length portions of the foot plate 12, including a toe portion 34, a heel portion 38, and an arched intermediate portion 40.

In embodiments, the shank plate 14 also has an elongate shape with top and bottom side surfaces 50 and 52, respectively, defining its length and width between opposing end edges 54 and 56 and opposing side edges 58 and 60. The top and bottom side surfaces 50 and 52 have contours defining an upper portion 62, an intermediate portion 64, and a lower portion 66 of the shank plate 14.

In embodiments, an attachment structure 70 attaches the shank plate 14 to the foot plate 12. In the attached configuration shown in FIG. 1, the upper portion 62 of the shank plate 14 is oriented vertically for connection with another component of a prosthetic leg, such as a socket or a knee joint (not shown). The lower portion 66 of the shank plate 14 overlies the intermediate and toe portions 40 and 34 of the foot plate 14. The curvature of the intermediate portion 64 of the shank plate 14 provides a flexible transition between the upper portion 62 and the lower portion 66.

In embodiments, both the foot plate 12 and the shank plate 14 are formed of a composite material including reinforcing fibers embedded in a resin binder. In an exemplary embodiment, the fibers are aligned primarily unidirectionally lengthwise of each plate 12 and 14.

In an embodiment, the attachment structure 70 also is formed of a composite material including reinforcing fibers embedded in a resin binder. The fibers in the attachment structure 70 are primarily aligned unidirectionally along a transverse axis 75 normal to the lengthwise directions of the foot and shank plates 12 and 14. The fibers in the attachment structure 70 thus reach through the plates 12 and 14 primarily in a common direction through the thickness of the plates 12 and 14 instead of along the lengths of the plates 12 and 14.

As shown in FIG. 2, in embodiments, the foot structure 10 includes additional parts, such as layers 80 of composite weave material. One layer 80A of composite weave material is provided to overlie the top surface 50 of shank plate 14. Another layer of composite weave material 80B is provided to underlie the bottom surface 32 of the foot plate 12. In embodiments, additional parts also include layers of peel ply film 82A, 82B, 82C, 82D that are placed between the plates 12 and 14 and surrounding parts of mold 86, which in embodiments include upper part 86A, heel part 86B, and sole part 86C.

Figure 3:
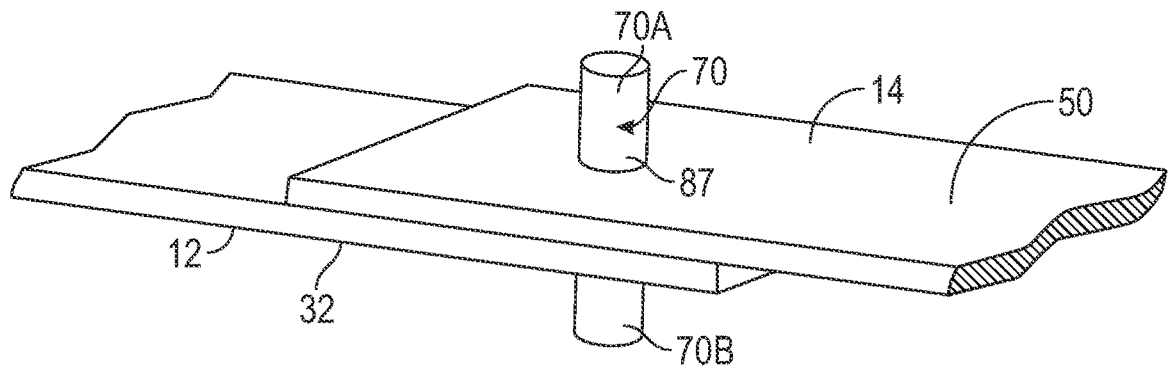
FIG. 3 is a detail showing the attachment structure inserted through the shank plate and the foot plate of the composite prosthetic foot structure prior to molding.

As shown in FIG. 2, in embodiments, the foot plate 12, the shank plate 14, and an intervening layer 82A of peel ply film are provided with apertures 87. As shown in FIG. 3, in embodiments the attachment structure 70 takes the form of a sheet of composite material, such as the composite material used to form the foot plate 12 and/or the shank plate 14, that is rolled into the shape of a cylinder. When the components of FIG. 2 are being placed together in the mold, the apertures 87 are aligned on the transverse axis 75 (FIG. 4), and the cylindrical attachment structure 70 is inserted thought the aligned apertures 87. In embodiments, the cylindrical attachment structure 70 is shaped such that upper and lower portions 70A, 70B, respectively, protrude above the top surface 50 of the shank plate 14 and below the bottom surface 32 of the foot plate 12 and form the top and bottom flattened end portions 90, 92, respectively, described below with reference to FIG. 4, interconnected by a cylindrical central shaft 89.

In an embodiment depicted in FIG. 2, the peel ply film 82D, composite weave material layer 80A, shank plate 14, peel ply films 82 B, 82C, foot plate 12, composite weave material layer 80B, and peel ply film 82C are layered as shown and the mold parts 86A, 86B, and 86C are brought together and the composition heated. This causes the composite weave material layers 80A, 80B to bond to the shank plate 14 and foot plate 12, the shank plate to bond to the foot plate 12 along seam 100 (FIG. 4), and the shank plate and foot plate to conform to the contours of the mold parts 86A, 86B, and 86C, resulting in the shape of the composite prosthetic foot structure 10 shown in FIG. 1.

In an embodiment, this molding process also deforms the attachment structure 70 into the configuration shown in FIG. 4, in which the top and bottom portions 70A, 70B are compressed and flatten into flattened or flared top and bottom end portions 90 and 92, respectively. As indicated schematically in FIG. 4, in an exemplary embodiment, the reinforcing fibers in the top and bottom end portions 90 and 92 diverge radially outward over the top surface 50 of the shank plate 14 and the bottom surface 32 of the foot plate 12. In an embodiment, the top and bottom surfaces 50 and 32 of the plates 14 and 12, respectively, are provided with recesses 95 that receive the deflected end portions 90 and 92 of the attachment structure 70, as shown in FIG. 4, and thereby to avoid a surface bulge from the top surface 50 and bottom surface 32 of the shank plate 14 and foot plate 12 at each of those locations.

In another embodiment, the deflected top and bottom end portions 90 and 92 are pressed onto the top and bottom surfaces 50 and 32 without the recesses 95. In embodiments, the overlying and underlying layers 80A, 80B, respectively, of composite weave material also help to provide smooth surfaces over the deflected end portions 90 and 92 of the attachment structure 70.

The resin materials in the plates 12 and 14, the composite weave layers 80A, 80B, and the attachment structure 70 are cured together against the mold parts 86A, 86B, and 86C. In an embodiment, a single curing process bonds all the adjoining composite materials together. This forms a seam 100 along which the shank plate 14 is bonded to the foot plate 12. The mold parts 86A-86C are shaped such that the seam 100 extends rearward from the forward ends 28, 56 of the plates 12 and 14 until the forward end of a layer 82A of peel ply film blocks the formation of a bond where it extends between the shank plate 14 and the foot plate 12.

The layers 82B and/or 82A of peel ply film optionally are removed to expose a gap 105 (FIG. 4) across which the bottom surface 52 of the shank plate 14 is spaced apart from the top surface 30 of the foot plate 12. The gap 105 enables the shank plate 14 and the foot plate 12 to deflect independently of one another at that location. The optional removal of the layer 82D of peel ply film does not affect the mechanical characteristics of the prosthetic foot structure 10 and improves the cosmetic appearance of the final part.

During use of the composite prosthetic foot structure 10 by a wearer, when the wearer places their weight on the prosthetic structure 10 and removes their weight in, for example, a walking gait, the foot plate 12 and shank plate 14 deflect toward and away from each other across the gap 105. Stresses can concentrate at the rear end 106 (FIG. 4) of the seam 100 where the foot plate 12 and shank plate 14 cannot flex independently. However, the attachment structure 70 is located to bear the load of these stresses to prevent separation of the plates 12 and 14 at the seam 100. Specifically, if the seam 100 were extended to reach rearward past the attachment structure 70, a rearward extending section of the seam 100 might rupture as the foot plate 12 and shank plate 14 repeatedly deflect away from one another during use.

Figure 5:
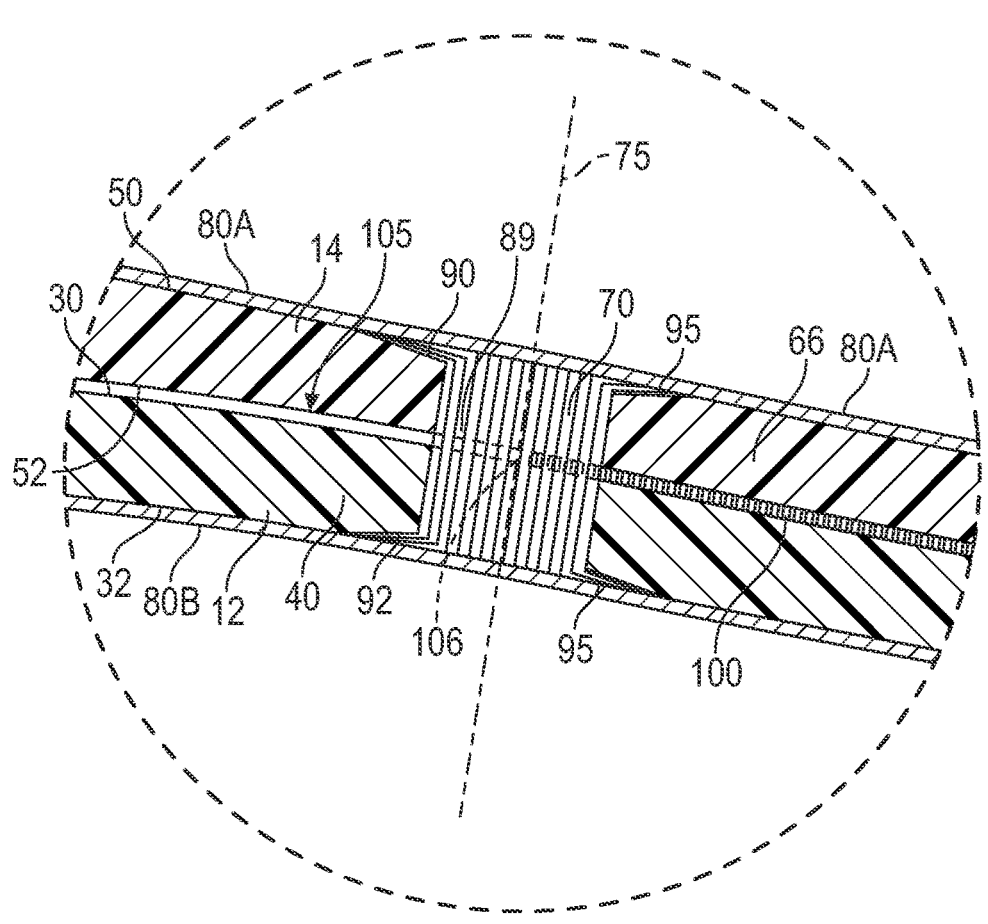
FIG. 5 is an enlarged view of an alternative attachment structure of the composite prosthetic foot structure of FIG. 1.

For this reason, in embodiments the attachment structure 70 is located at least partially to the rear of the seam 100 so that the seam 100 does not reach rearward (to the left in FIGS. 4 and 5) past the attachment structure 70. In the embodiment shown in FIGS. 1 and 2, the attachment structure 70 is located entirely to the rear of the seam 100, so that the gap 105 is present on both sides of the attachment structure. In the embodiment shown in FIG. 5, the attachment structure is located partially within, and extends through the gap 105 and is located partially within and extends through the seam 100, so that the rear end 106 of the seam is located at the attachment structure. In each of these exemplary embodiments, the fibers in the attachment structure 70 are primarily aligned unidirectionally with the transverse axis 75 along their lengths reaching through the foot plate 12, the gap 105, the shank plate 14, and for the embodiment of FIG. 5, through the seam 100.

Figure 6:
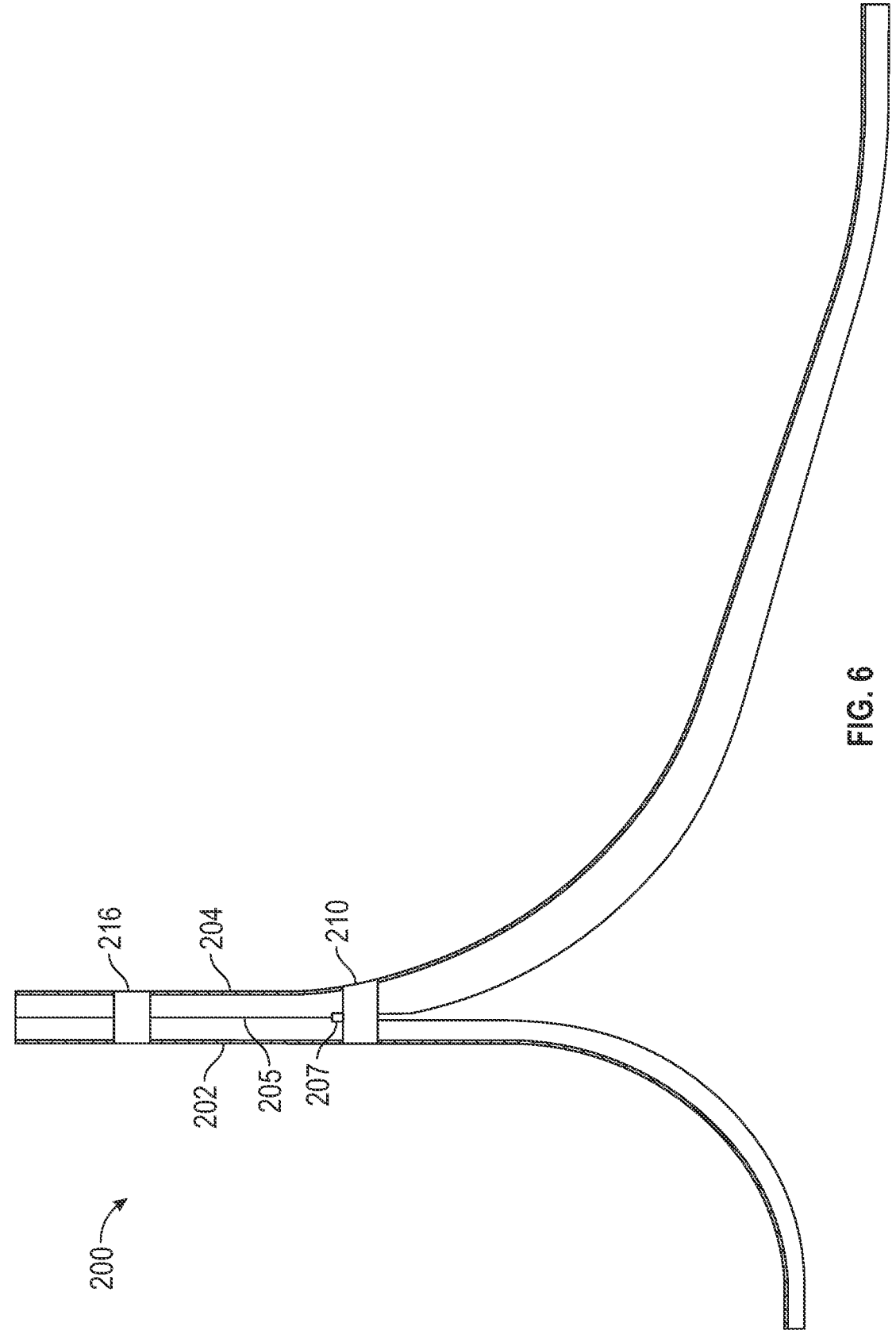
FIG. 6 is a schematic side elevation of an alternative embodiment of the disclosed composite prosthetic foot structure.

In the alternative embodiment of FIG. 6, a plate assembly in a prosthetic foot structure 200 includes first and second plates 202 and 204. These plates 202 and 204 have composite compositions substantially the same as the composite compositions of the plates 12 and 14 described above. The plates 202 and 204 are joined along a seam 205 that terminates at a gap 207. The foot structure 200 further includes an attachment structure 210 having substantially the same composition and structural configuration as the attachment structure 70 described above. The attachment structure 210 thus reaches through the plates 202 and 204 and across the gap 207 to prevent separation of the plates 202 and 204 at the seam 207. One or more additional attachment structures 216 may also be provided.

Figure 7:
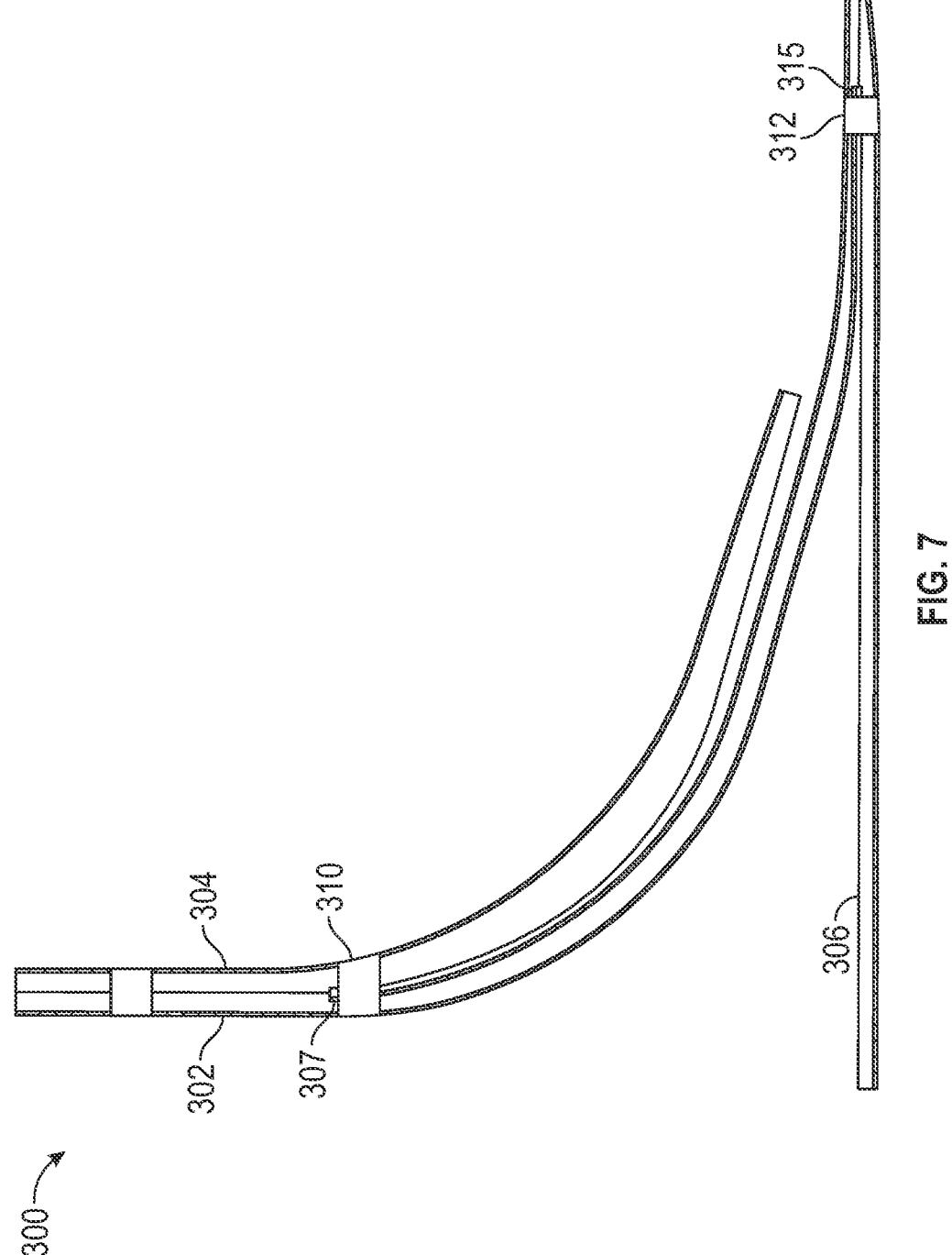
FIG. 7 is a schematic side elevation of a second alternative embodiment of the disclosed composite prosthetic foot structure.
Figure 8:
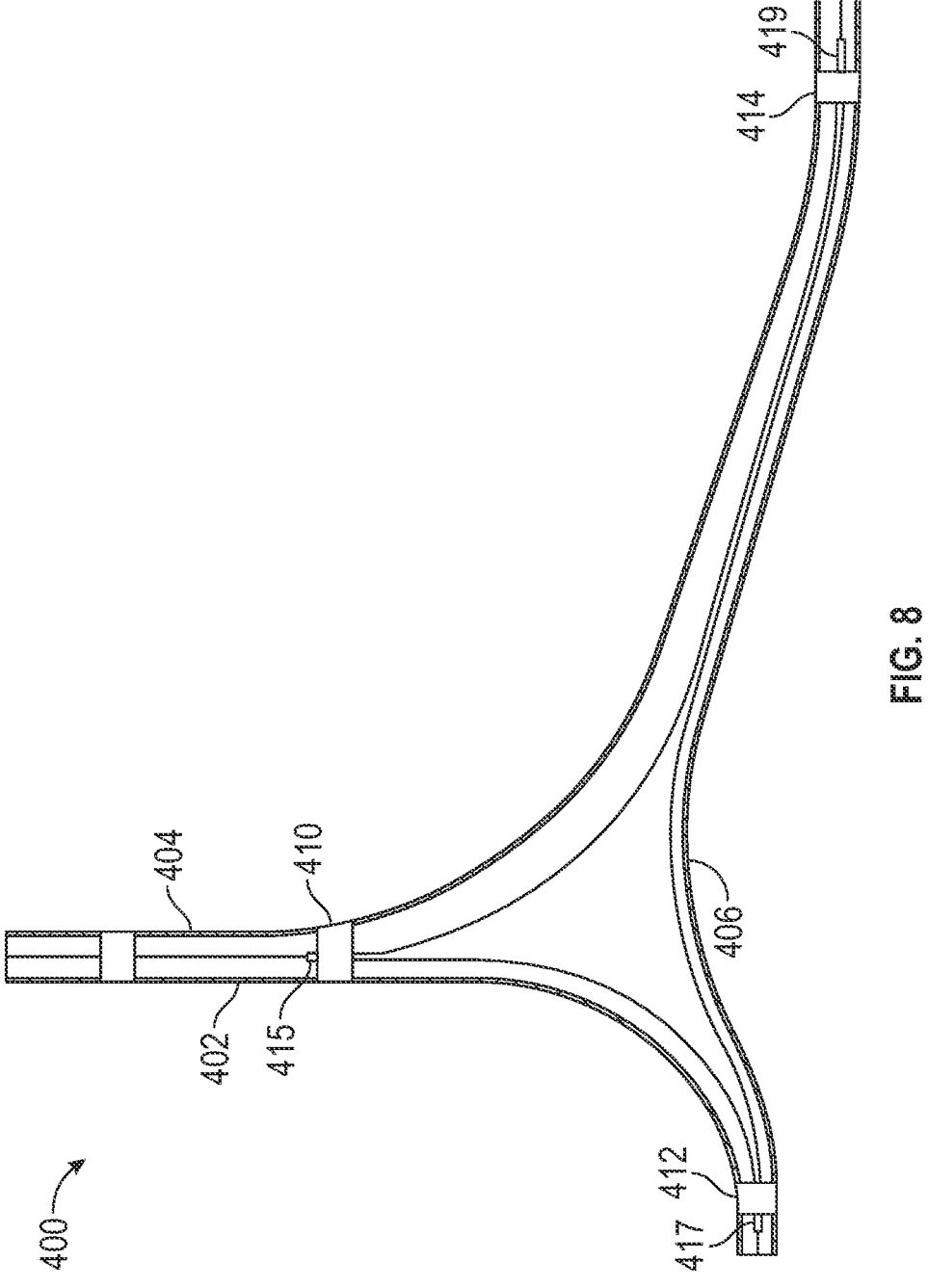
FIG. 8 is a schematic side elevation of a third alternative embodiment of the disclosed composite the prosthetic foot structure.

Second and third alternative embodiments are shown in FIGS. 7 and 8, respectively. In the embodiment of FIG. 7, the foot structure 300 includes three composite plates 302, 304, and 306 attached together by two composite attachment structures 310 and 312. One of these attachment structures 310 reaches through the plates 302, 304 and a gap 307 between the plates 302, 304. The other attachment structure reaches through the plates 302, 306 and a gap 315 between those plates 302, 306. In the embodiment of FIG. 8, the foot structure 400 similarly includes three composite plates 402, 404, and 406 with three composite attachment structures 410, 412 and 414 at respective gaps 415, 417, and 419. One or more additional attachment structures also may be provided in the embodiments of FIGS. 7 and 8, as shown.

Figures 9, 10, 11:
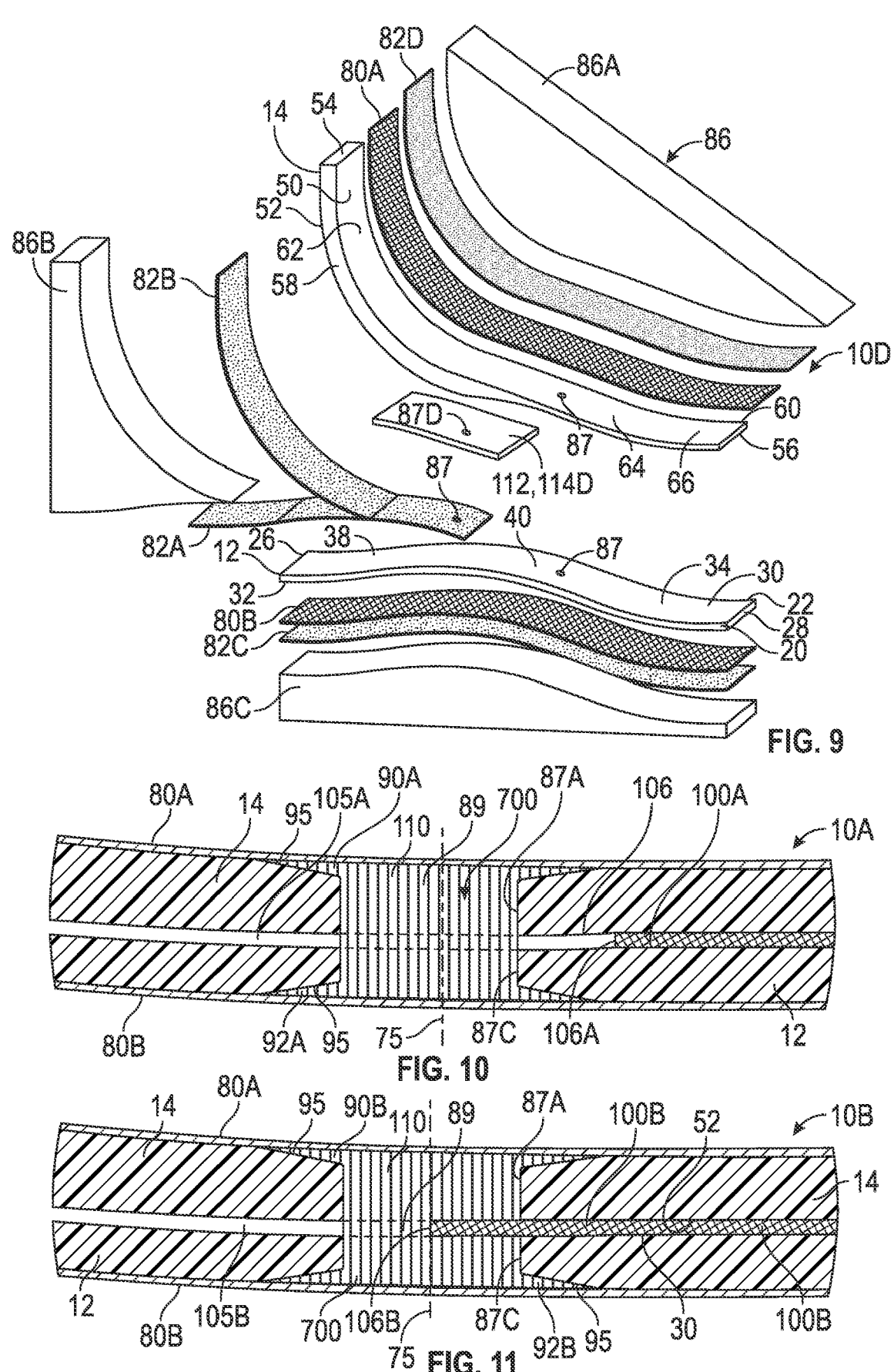
FIG. 9 is an exploded view of the embodiment of the prosthetic foot structure of FIG. 10D, shown between mold parts.
FIG. 10 is a detail showing the attachment structure of a fourth alternative embodiment of the disclosed prosthetic foot structure.
FIG. 11 is a detail showing the attachment structure of a fifth alternative embodiment of the disclosed prosthetic foot structure.

As shown in FIG. 10, a fourth embodiment of the composite prosthetic foot structure, generally designated 10A, is identical to the embodiment of FIGS. 1 and 4, except as follows. The attachment structure 700 is made up of fibers 110 without a supporting matrix of a resin. In an embodiment, the fibers are oriented as shown in FIG. 10 to extend through openings 87A, 87C of the shank plate 14 and foot plate 12, respectively, and across the gap 105A. Thus, the prosthetic foot 10A includes a foot plate 12 having a toe portion 34 (FIG. 1) and a heel portion 38. The shank plate 14 is bonded to the foot plate 12 along a seam 100A that extends from the toe portion 34 rearward toward the heel portion 38 to terminate at an end 106A. The shank plate 14 is separated from the foot plate 12 forming a gap 105A between the foot plate and shank plate that extends rearward from the end 106A of the seam.

An attachment structure 700 attaches the foot plate 12 to the shank plate 14. In embodiments, the attachment structure 700 includes fibers 110, and consists or consists essentially of fibers 110, extending through the shank plate 14, the gap 105A, and the foot plate 12. In the embodiment of the prosthetic foot 10A of FIG. 10, the fibers 110 of the attachment structure 700 extend through the gap 105A but not through the seam 100A. The end 106A of the seam 100A terminates along the lengths of the shank plate 14 and foot plate 12 forward of the attachment structure 700.

A fifth embodiment of the prosthetic foot system, generally designated 10B and shown in FIG. 11, is identical to the embodiments 10, 10A of the prosthetic foot systems shown in FIGS. 1 and 10, respectively, except as follows. The end 106B of the seam 100B extends from the toe portion 34 of the foot plate 12 (FIG. 1) rearward between, and joins, the top surface 30 of the foot plate and bottom surface 52 of the shank plate 14 to terminate at a point along the length of the shank plate that coincides with the location of the attachment structure 700, so that the end 106B of the seam 100B is transversely aligned along a length of the prosthetic foot 10B with the attachment structure. With the embodiment of the prosthetic foot 10B of FIG. 11, the fibers 110 of the attachment structure 700 extend through the gap 105B and also extend through the seam 100B. The top end portion 90B and bottom end portion 92B of the fibers 110 are bent or flare radially outward from the transverse axis 75 of the cylindrical central shaft 89 of the attachment structure.

An exemplary embodiment of the prosthetic foot, generally designated 10B, is shown in FIG. 11. In this embodiment, the end 106B of the seam 100B coincides with, or approximately with, a midpoint of the attachment structure 700, coinciding with, or approximately with, the transverse axis 75. In other embodiments, the end 106B of the seam 100B terminates coinciding transversely with a portion of the attachment structure 700 forward toward the toe portion 34 of the transverse axis 75 or coinciding transversely with a portion of the attachment structure 700 rearward of the transverse axis 75 toward the heel portion 38.

Figures 12, 13, 14, 15:
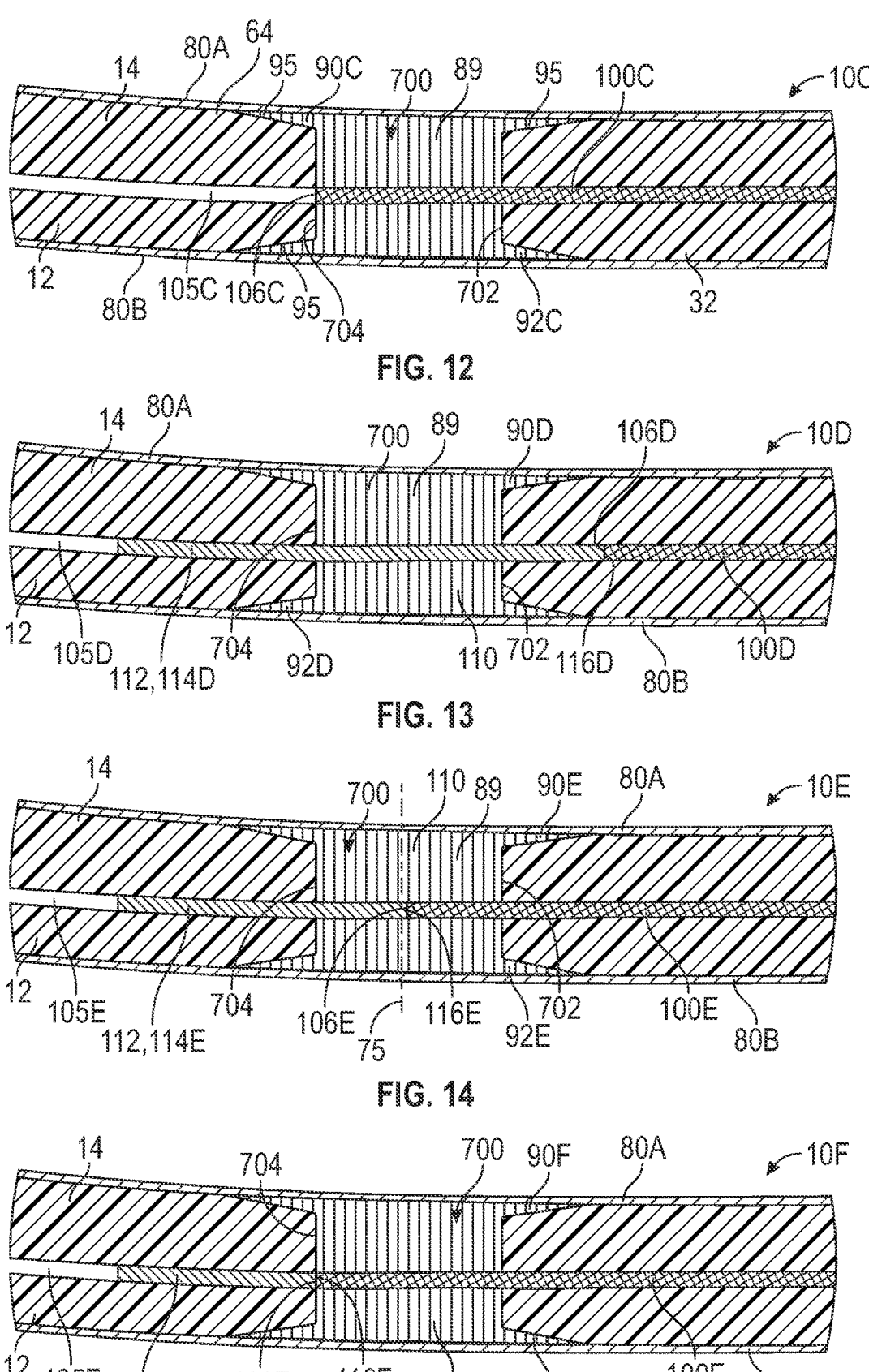
FIG. 12 is a detail showing the attachment structure of a sixth alternative embodiment of the disclosed prosthetic foot structure.
FIG. 13 is a detail showing the attachment structure of a seventh alternative embodiment of the disclosed prosthetic foot structure.
FIG. 14 is a detail showing the attachment structure of a eighth alternative embodiment of the disclosed prosthetic foot structure.
FIG. 15 is a detail showing the attachment structure of a ninth alternative embodiment of the disclosed prosthetic foot structure.

In the embodiment of the prosthetic foot, generally designated 10C, shown in FIG. 12, the cylindrical central shaft 89 of the attachment structure 700 has a forwardmost leading edge 702 toward the toe portion 34 (FIG. 1), a rearmost trailing edge 704 toward the heel portion 38, and the cylindrical shaft 89 extends through the shank plate 14, the seam 100C, and the foot plate 12. The flared top portion 90C overlies the top surface 64 of the shank plate 14, and the flared bottom portion 92C overlies a bottom surface 32 of the foot plate 12. The end 106C of the seam 100C is transversely aligned along a length of the prosthetic foot between the leading edge 702 and the trailing edge 704. In the exemplary embodiment shown, the end 106C of the seam 100C coincides longitudinally with, or approximately with, but not rearward of, the trailing edge 704 of the cylindrical central shaft 89 of the attachment structure 700.

In an embodiment of the prosthetic foot, generally designated 10D, shown in FIGS. 9 and 13, a flexible material 112 is placed in the gap 105D formed between the shank plate 14 and the foot plate 12. As shown in FIG. 9, in embodiments the flexible material may take the form of a strip 114D that extends a width of the foot plate 12 and the matching width of the shank plate 14. In embodiments, the flexible material 112 is selected from natural rubber, synthetic rubber, nitrile rubber, silicone rubber, a urethane rubber, chloroprene rubber, ethylene rubber, and vinyl acetate rubber.

In the exemplary embodiment of FIG. 13, the strip 114D of flexible material 112 extends along the gap 105D from a point forward of the leading edge 702 of the cylindrical central shaft 89 of the attachment structure 700 toward the toe portion 34 (FIG. 1) of the prosthetic foot 10D rearward of the attachment structure toward the heel portion 38. In an embodiment, the flexible material 112 fills the gap 105D adjacent and, in embodiments, contacting the end 106D of the seam 100D. The strip 114D extends rearward of the end 106D to terminate at a point past and rearward of the trailing edge 704 of the cylindrical central shaft 89 of the attachment structure 700.

In this embodiment 10D, the flexible material 112 contacts the end 106D of the seam 100D forward of the attachment 700 structure toward the toe portion 34 such that the fibers 110 extend through the strip 114D of flexible material 112 in the gap 105D. As shown in FIG. 9, in embodiments, the strip 114D includes an aperture 87D through which the fibers 110 of the attachment structure 700 extend.

As shown in FIG. 14, in an embodiment of the prosthetic foot, generally designated 10E, the end 106E of the seam 100E is transversely aligned along a length of the prosthetic foot with the attachment structure 700 and the flexible material 112 contacts the end of the seam such that the fibers 110 extend through the flexible material in the gap 105E and through the seam 100E. In embodiment shown in FIG. 14, the end 106E coincides or approximately coincides with the transverse axis 75, so that the forward end 116E of the flexible strip 114E meet at or approximately at the transverse axis 75. In other embodiments, the forward end 116E and the end 106E meet between the transverse axis 75 and the leading edge 702 of the cylindrical central shaft 89 or between the transverse axis and the trailing edge 704.

In another embodiment of the prosthetic foot, generally designated 10F, shown in FIG. 15, The seam 100F extends from the toe portion 34 rearward and terminates so that the end 106F of the seam coincides longitudinally with the trailing edge 704 of the cylindrical central shaft 89 of the attachment structure 700. The strip 114F of flexible material 114 fills the gap 105F between the shank plate 14 and the foot plate 12 such that the forward end 116F is adjacent and abuts the end 106F of the seam 100F at the trailing edge 704.

As shown in FIGS. 13-15, the performance characteristics of the prosthetic foot 10D-10F, such as the compressibility of the shank plate 14 against the foot plate 12 and the resiliency of the shank plate and foot plate engagement, can be varied by varying the length and placement of the flexible material 112 within the gap 105D-105F rearward of the seam 100D-100F. In each embodiment of the prosthetic foot 10D-10F, the flexible material 112 completely fills and extends along the gap 105D-105F for a selected distance rearward of the attachment structure 700 toward the heel portion 38 of the shank plate 12. In embodiments, the strip 114D-114F extends selected distances along the gap 105D-105F up to the point rearward of the attachment structure 700 where the shank plate 14 and the foot plate 12 do not deflect to contact each other during use. And in embodiments, the flexible material 112 fills the gap 105D-105F adjacent and contacting the end 106D-106F of the seam 100D-100F.

In the prosthetic foot 10D of the embodiment of FIG. 13, the flexible material 112 contacts the end 106D of the seam 100D forward of the attachment structure 700 toward the toe portion 34 such that the fibers 110 extend through the flexible material in the gap 105D. In the prosthetic foot 10E of the embodiment of FIG. 14, the end 106E of the seam 100E is transversely aligned along a length of the prosthetic foot with the attachment structure 700 and the flexible material 112 contacts the end of the seam such that the fibers 110 extend through both the flexible material in the gap 105E and through the seam. In a particular embodiment, the flexible material 112 and the seam 110E abut at or at approximately the transverse axis 75, and in other embodiments forward or rearward of it. Thus, in the embodiments 10D and 10E of the prosthetic foot depicted in FIGS. 13 and 14, the flexible material 112 extends rearward from the end 106D, 106E of the seam 100D, 100E such that the attachment structure 700 passes through the flexible material.

In the embodiment of the prosthetic foot 10F of FIG. 15, the end 106F of the seam 100F transversely coincides with a rearmost trailing edge 704 of the attachment structure 700 toward the heel portion 38, and the flexible material 112 fills the gap 105F adjacent and contacting the end of the seam and extends rearward toward the heel portion 38.

In embodiments, the length of the strip 114D-114F of flexible material, the composition of the flexible material, and the of the forward end 116D-116F along the length of the prosthetic foot are selected to vary the resiliency and

9 | 10 flexure characteristics of the prosthetic foot 10D-10F. The location of the strip 114D-114F also provides a reduction in the noise that might otherwise result from contact between the shank plate 14 and foot plate 12 during walking by a user.

In each of the embodiments 10D-10F of the prosthetic foot, individual ones of the fibers 110 are oriented to extend longitudinally and continuously through the shank plate 14, the gap 105A-105F, the seam 110A-110F and/or the flexible strip 114D-114F, and the foot plate 12. In embodiments, the fibers 110A-110F are made of a material selected from one or more of steel, carbon, glass, nylon, an aramid, and polyethylene.

In embodiments, the fibers 110 are angled radially outward from the cylindrical central shaft 89 to form the flared top portion 90A-90F and the flared bottom portion 92A-92F of the attachment portion 700. In embodiments, flared top portion 90A-90F and the flared bottom portion 92A-92F of the attachment portion 700 are positioned within recesses 95 formed in the top surface 50 and bottom surface 32 of the shank portion 14 and foot portion 12, respectively. In embodiments, the entire top surface 50 and bottom surface 32, including the flared top portion 90A-90F and the flared bottom portion 92A-92F, are covered by the layers 80A, 80B, respectively, of composite weave material.

In sum, the exemplary embodiments 10A-10F of the disclosed prosthetic foot shown in FIGS. 9-15 comprise: a foot plate 12 having a toe portion 34 and a heel portion 38 and a shank plate 14 bonded to the foot plate along a seam 100A-100F that extends from the toe portion rearward toward the heel portion to terminate at an end 106A-106F. The shank plate 14 is separated from the foot plate 12 forming a gap 105A-105F between the foot plate and shank plate extending rearward from the end 106A-106F of the seam. An attachment structure 700 attaches the foot plate 12 to the shank plate 14, wherein the attachment structure includes a central shaft 89 of fibers 110 extending through the shank plate, the seam (in the embodiments of FIGS. 9, 10, 11, 12, 14, and 15), and the foot plate. An end 106A-106F of the seam 100A-100F is transversely aligned along a length of the prosthetic foot 10A-10F with a rearmost trailing edge 704 of the cylindrical central shaft 89.

In embodiments, the prosthetic foot 10D-10F further comprises a flexible material 112 in the gap 105D-105F contacting and extending rearward from the trailing edge 106D-106F of the seam 100D-100F. In embodiments, the foot plate 12 and the shank plate 14 each are discrete plates made of a composite, such as fiber reinforced resin or carbon fiber reinforced plastic (CFRP).

An exemplary embodiment of a method of making a prosthetic foot is shown in FIG. 9 with reference to the embodiment 10D of the prosthetic foot shown in FIG. 13. The method includes placing a first layer 82C of peel ply material on a sole mold part 86C, placing a first layer 80B of composite weave on the first layer of peel ply material, and placing a foot plate 12 on the first layer of composite weave, the foot plate having a toe portion 34 and a heel portion 38. Second and third layers 82A, 82B, respectively of peel ply material are placed over and under a heel mold part 86B. A strip 114D of flexible material 112 is placed over a portion of the second layer 82A of peel ply material and a shank plate 14 is placed over the portion of the second layer 82A of peel ply material and the strip 114D of flexible material 112.

An attachment structure 700 is inserted through the shank plate 14, the strip 114D of flexible material 112, the portion of the second layer 82A of the peel ply material, and the foot plate 12. The attachment structure 700 includes fibers 110 extending through the shank plate 14, the flexible material 112, and the foot plate 12. A second layer 80A of composite weave is placed on a top surface 50 of the shank plate 14, and a fourth layer 82D of peel ply material is placed over the second layer 80A of composite weave. An upper mold part 86A is placed over the fourth layer 82D of peel ply material.

The first layer 82C of peel ply material, the first layer 80B of composite weave, the foot plate 12, second and third layers 82A, 82B, respectively, of peel ply material, the strip 114D of flexible material 112, the shank plate 14, the second layer 80A of composite weave, the fourth layer 82D of peel ply material, and the attachment structure 700 are compressed between the upper mold part 86A, the heel mold part 86B, and the sole mold part 86C to bond the shank plate 14 to the foot plate 12 to form a seam 100D therebetween that extends forward of the attachment structure 700 toward the toe portion 34. The attachment structure 700 includes fibers 110 extending through the shank plate 14, the strip 114D of flexible material 112, and the foot plate 12, thereby forming a flared top portion 90D that overlies a top surface 50 of the shank plate and a flared bottom portion 92D that overlies a bottom surface 32 of the foot plate 12 and also forms a gap 105D between the shank plate and the foot plate that extends rearward of the flexible strip 114D toward the heel portion 38.

The various embodiments 10, 10A-10F of the prosthetic foot described above and illustrated in the Figures provide a rugged, resilient, and yet lightweight prosthetic foot, the components of which can be customized easily to suit the preferences of a user regarding resiliency, flexure, and feel. The inclusion of the described attachment structure 700 made of elongate fibers 110 secures the shank plate 14 to the foot plate 12 and prevents failure of the seam 100, 100A-100F, yet does not restrict the flexibility of the overall foot 10, 10A-10F.

While the forms of apparatus and methods herein described constitute preferred embodiments of the disclosed composite prosthetic foot structure, it is to be understood that the invention is not limited to these precise forms of apparatus and methods, and that changes may be made therein without departing from the scope of the invention.

What is claimed is:

1. A prosthetic foot, comprising:
   a foot plate having a toe portion and a heel portion;
   a shank plate bonded to the foot plate along a seam that extends from the toe portion rearward toward the heel portion and terminates at an end, the shank plate separated from the foot plate by a gap that extends rearward from the end of the seam; and
   an attachment structure attaching the foot plate to the shank plate, wherein the attachment structure includes fibers extending through at least the shank plate and the foot plate;
   wherein the end of the seam is transversely aligned along a length of the prosthetic foot with the attachment structure such that the fibers also extend through the seam.

2. The prosthetic foot of claim 1, wherein the attachment structure includes a central shaft that has a forwardmost leading edge toward the toe portion, a rearmost trailing edge toward the heel portion, and extends through at least the shank plate, the seam, and the foot plate.

3. The prosthetic foot of claim 2, wherein the end of the seam is transversely aligned along a length of the prosthetic foot between the forwardmost leading edge and the rearmost trailing edge.

4. The prosthetic foot of claim 2,
    wherein the end of the seam is transversely aligned along the length of the prosthetic foot with the rearmost trailing edge of the central shaft.

5. The prosthetic foot of claim 4, further comprising a flexible material in the gap contacting and extending rearward from the trailing edge of the central shaft.

6. The prosthetic foot of claim 2, wherein the attachment structure comprises a flared top portion that overlies a top surface of the shank plate and a flared bottom portion that overlies a bottom surface of the foot plate.

7. The prosthetic foot of claim 6, wherein ends of the fibers are angled radially outward from the central shaft to form the flared top portion and the flared bottom portion.

8. The prosthetic foot of claim 1, wherein the fibers are made of a material selected from one or more of steel, carbon, glass, nylon, an aramid, and polyethylene.

9. The prosthetic foot of claim 1, wherein the foot plate and the shank plate each are discrete plates made of a composite.

\* \* \* \* \*